US009351936B2

(12) United States Patent
Gao et al.

(10) Patent No.: US 9,351,936 B2
(45) Date of Patent: May 31, 2016

(54) NICOTINE LOZENGE

(71) Applicant: ALTRIA CLIENT SERVICES LLC, Richmond, VA (US)

(72) Inventors: Feng Gao, Midlothian, VA (US); Diane L. Gee, Chesterfield, VA (US); Phillip M. Hulan, Midlothian, VA (US); Shuzhong Zhuang, Glen Allen, VA (US); William J. Burke, Nashville, TN (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 14/506,093

(22) Filed: Oct. 3, 2014

(65) Prior Publication Data

US 2015/0098996 A1  Apr. 9, 2015

Related U.S. Application Data

(60) Provisional application No. 61/886,386, filed on Oct. 3, 2013.

(51) Int. Cl.

| | |
|---|---|
| A61K 9/20 | (2006.01) |
| A61K 31/465 | (2006.01) |
| A61K 9/00 | (2006.01) |
| B29C 47/00 | (2006.01) |
| B29C 47/10 | (2006.01) |

(52) U.S. Cl.
CPC ............. *A61K 9/2059* (2013.01); *A61K 9/0056* (2013.01); *A61K 9/2095* (2013.01); *A61K 31/465* (2013.01); *B29C 47/0066* (2013.01); *B29C 47/1081* (2013.01); *B29C 2793/009* (2013.01); *B29C 2793/0009* (2013.01)

(58) Field of Classification Search
CPC . A61K 9/2059; A61K 31/465; A61K 9/0056; A61K 9/2095; B29C 47/0066; B29C 2793/009; B29C 2793/0009; B29C 47/1081
See application file for complete search history.

(56) References Cited

U.S. PATENT DOCUMENTS

| | | | |
|---|---|---|---|
| 2,162,738 A | 6/1939 | McCoy | |
| 3,139,436 A | 6/1964 | Bicking | |
| 3,396,735 A | 8/1968 | Bethmann et al. | |
| 4,153,063 A | 5/1979 | Roselius et al. | |
| 4,448,208 A | 5/1984 | Friedrich et al. | |
| 4,516,590 A | 5/1985 | Teng | |
| 4,528,993 A | 7/1985 | Sensabaugh et al. | |
| 4,660,577 A | 4/1987 | Sensabaugh et al. | |
| 4,848,373 A | 7/1989 | Lenkey | |
| 4,987,907 A | 1/1991 | Townend | |
| 5,236,719 A | 8/1993 | Meyers et al. | |
| 5,284,163 A * | 2/1994 | Knudsen | A23G 4/068 131/270 |
| 5,372,149 A | 12/1994 | Roth et al. | |
| 5,380,717 A | 1/1995 | Ohkuma et al. | |
| 5,410,035 A | 4/1995 | Wakabayashi et al. | |
| 5,487,792 A | 1/1996 | King et al. | |
| 6,203,842 B1 | 3/2001 | Reddy | |
| 7,798,151 B2 | 9/2010 | Krukonis et al. | |
| 2004/0118422 A1 | 6/2004 | Lundin et al. | |
| 2005/0053665 A1* | 3/2005 | Ek | A61K 9/0056 424/488 |
| 2005/0178398 A1 | 8/2005 | Breslin et al. | |
| 2006/0171994 A1* | 8/2006 | Dupinay | A61K 9/0056 424/440 |
| 2007/0144544 A1* | 6/2007 | Cai | A23G 3/36 131/271 |
| 2008/0209586 A1 | 8/2008 | Nielsen et al. | |
| 2011/0139164 A1 | 6/2011 | Mua et al. | |
| 2011/0200670 A1* | 8/2011 | Thakkar | A61K 9/0056 424/465 |
| 2012/0053108 A1* | 3/2012 | Glenn, Jr. | A61L 27/50 510/296 |
| 2013/0186418 A1 | 7/2013 | Feng et al. | |
| 2013/0206150 A1 | 8/2013 | Duggins et al. | |
| 2015/0020818 A1 | 1/2015 | Gao et al. | |

FOREIGN PATENT DOCUMENTS

| | | |
|---|---|---|
| WO | 2009/134947 | 11/2009 |
| WO | 2010/044736 | 4/2010 |

OTHER PUBLICATIONS

Y. Gonnissen, et al, Development of Directly Compressible Powders via Co-Spraying, 67 Eur. J Pharma. Biopharma. 220 (2007).*
International Search Report and Written Opinion in International Application No. PCT/US2014/059148, mailed Dec. 12, 2014, 9 pages.
Tso (1999, Chapter 1 in Tobacco, Production, Chemistry and Technology, Davis & Nielsen, eds., Blackwell Publishing, Oxford).

* cited by examiner

*Primary Examiner* — Sean Basquill
(74) *Attorney, Agent, or Firm* — Fish & Richardson P.C.

(57) ABSTRACT

A nicotine lozenge provided herein includes a body that is partially or wholly receivable in an oral cavity. The body includes a soluble-fiber matrix and nicotine or a derivative thereof dispersed in the soluble-fiber matrix. In some cases, a nicotine lozenge provided herein includes at least 40 weight percent of soluble fiber. In some cases, soluble fiber in a nicotine lozenge provided herein can include maltodextrin. The nicotine lozenge is adapted to release the nicotine or a derivative thereof from the body when the body is received within the oral cavity of an adult consumer and exposed to saliva. A method of making nicotine lozenges provided herein includes forming a molten mixture of at least 40 weight percent soluble fiber, nicotine, and less than 15 weight percent water while maintaining a mixture temperature of less than 150° C. and portioning the molten mixture into a plurality of nicotine lozenges. In some cases, the ingredients can be mixed to form the molten mixture in an extruder.

35 Claims, 9 Drawing Sheets

NICOTINE LOZENGE

CROSS REFERENCE TO RELATED APPLICATIONS

This application claims the benefit of priority under 35 U.S.C. §119(e) to U.S. Application No. 61/886,386 filed Oct. 3, 2013. The prior application is incorporated herein by reference in its entirety.

TECHNICAL FIELD

This document relates to nicotine lozenges and methods for making nicotine lozenges. For example, a nicotine lozenge can include nicotine within a soluble-fiber matrix (e.g., maltodextrin).

BACKGROUND

Tobacco can be enjoyed by adult tobacco consumers in a variety of forms. Smoking tobacco is combusted and the aerosol either tasted or inhaled (e.g., in a cigarette, cigar, or pipe). Smokeless tobacco products are not combusted and include: chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally.

Nicotine is a component of various tobacco products. Over the years, however, various methods and systems have been developed for providing nicotine to adult consumers without the presence of tobacco plant tissue. Some ways tobacco-free nicotine is provided include transdermal patches, lozenges, and nicotine chewing gums.

Nicotine, or 3-(1-methyl-2-pyrrolidinyl)pyridine, is a tertiary amine with the following structure:

Under ambient conditions, nicotine is an oily, volatile, hygroscopic liquid that is sensitive to light and air. Chemical and physical properties of nicotine present a number of processing and stability issues. For example, because nicotine is volatile, it may evaporate during its incorporation into a gum or lozenge. In an effort to reduce potential processing and stability issues associated with the nicotine compound, a number of nicotine complexes have been developed. For example, one method includes the preparation of a complex of nicotine and an ion exchange resin. A well-known complex that is currently used in the commercially-available nicotine chewing gums is nicotine polacrilex, which is a complex of nicotine and the cation exchange resin AMBERLITE 164.

SUMMARY

A nicotine lozenge provided herein provides a satisfying tactile and/or flavor experience. A nicotine lozenge provided herein includes a body that is at least partially receivable in an oral cavity of an adult consumer. In some cases, a nicotine lozenge provided herein includes a body that is wholly receivable in an oral cavity. The body can include a soluble-fiber matrix and nicotine or a derivative thereof dispersed in the soluble-fiber matrix. In some cases, the body can include unbound nicotine. In some cases, a nicotine lozenge provided herein includes at least 40 weight percent of soluble fiber. In some cases, soluble fiber in a nicotine lozenge provided herein can include maltodextrin. A nicotine lozenge provided herein can be adapted to release the nicotine or a derivative thereof from the body when the body is received within the oral cavity of an adult consumer and exposed to saliva. A body of a nicotine lozenge provided herein can be a single phase structure. In some cases, the body of a nicotine lozenge provided herein can be amorphous.

A method of making nicotine lozenges provided herein includes forming a molten mixture of at least 40 weight percent soluble fiber, nicotine, and less than 15 weight percent water while maintaining a mixture temperature of less than 150° C. and portioning the molten mixture into a plurality of nicotine lozenges. In some cases, the ingredients can be mixed to form the molten mixture in an extruder, flattened into a sheet of a predetermined thickness as it leaves the extruder, and individual nicotine lozenges cut from the sheet before the sheet cools below the glass transition temperature range of the molten mixture. Unlike a traditional lozenge, which incorporates sugars or sugar alcohols that are heated to a temperature such that caramelization occurs, methods provided herein include heating the molten mixture to form a solution of nicotine and water (and optionally other ingredients) in the soluble fiber without significant crosslinking. In some cases, additional additives can be added that are dispersed within the soluble fiber matrix, but not in solution with the soluble fiber. Because nicotine degradation can be accelerated when exposed to elevated temperatures over extended periods of time, the temperature of a molten mixture provided herein can be maintained at a temperature of 150° C. or below over a residence time of five to ten minutes or less (for example if an extrusion process is utilized). In some cases, a molten mixture provided herein is heated to a temperature of between 80° C. and 150° C. In some cases, a molten mixture provided herein is heated to a temperature of between 100° C. and 110° C. When cooled below its glass transition temperature, a molten mixture provided herein solidifies into an amorphous, non-porous, soluble fiber matrix containing nicotine. Because the soluble fibers do not become cross-linked, the soluble fibers remain soluble and thus dissolve when placed in an adult consumer's mouth.

A nicotine lozenge body can be rigid and brittle. In some cases, a body provided herein can have a glass transition temperature greater than 37° C. In some cases, a body provided herein can have a glass transition temperature of between 50° C. and 120° C. In some cases, a body provided herein can have a glass transition temperature of between 80° C. and 100° C. In some cases, a body provided herein having 90 weight percent maltodextrin can have a glass transition temperature of approximately 98° C. A nicotine lozenge provided herein can have a coating over the body. In some cases, the body of a nicotine lozenge provided herein can be non-porous.

A nicotine lozenge body can include at least 40 weight percent of soluble fiber. In some cases, the nicotine lozenge body includes at least 50 weight percent of soluble fiber. In some cases, the nicotine lozenge body includes at least 60 weight percent of soluble fiber. In some cases, the nicotine lozenge body includes at least 70 weight percent of soluble fiber. In some cases, the nicotine lozenge body includes at least 75 weight percent of soluble fiber. In some cases, the nicotine lozenge body includes at least 80 weight percent of soluble fiber. In some cases, the nicotine lozenge body includes at least 85 weight percent of soluble fiber. In some cases, the nicotine lozenge body includes at least 90 weight percent of soluble fiber. In some cases, the nicotine lozenge body includes at least 95% weight percent of soluble fiber. In some cases, the soluble fiber can include maltodextrin, psylliums, inulin, arabinoxylans, cellulose, and many other plant components such as resistant starch, resistant dextrins, lignin, pectins, beta-glucans, and oligosaccharides or a combination thereof. In some cases, a nicotine lozenge body can include at least 40 weight percent maltodextrin. In some cases, the nicotine lozenge body includes at least 50 weight percent maltodextrin. In some cases, the nicotine lozenge body includes at least 60 weight percent maltodextrin. In some cases, the nicotine lozenge body includes at least 70 weight percent maltodextrin. In some cases, the nicotine lozenge body includes at least 75 weight percent maltodextrin. In some cases, the nicotine lozenge body includes at least 80 weight percent maltodextrin. In some cases, the nicotine lozenge body includes at least 85 weight percent maltodextrin. In some cases, the nicotine lozenge body includes at least 90 weight percent maltodextrin. In some cases, the nicotine lozenge body includes at least 95 weight percent maltodextrin.

In some cases, a nicotine lozenge provided herein can include a digestion-resistant soluble fiber (e.g., maltodextrins.) Suitable maltodextrins include those that are soluble in water up to 70% at 20° C., have a viscosity of about 15 cps for a 30% solution at 30° C., a DE in the range of about 6-16, and contain random α-1,2, α-1,3, α-1,4, β-1,2, β-1,3 and β-1,4 glucose linkages in addition to the normal α-1,4 glucose linkages found in partially hydrolyzed starch. See, e.g., U.S. Pat. Nos. 5,410,035; 5,380,717. For example, Fibersol®-2 is a maltodextrin of DE 6-10 processed from corn starch using hydrochloric acid and enzymes, which can be used as the soluble fiber in a nicotine lozenge provided herein. Fibersol®-2 is partially indigestible because human digestive enzymes are incapable of digesting β 1,2, β 1,3 and β 1,6 glucose bonds. See, e.g., U.S. Pat. No. 6,203,842. Other starch sources such as potato, rice, wheat, barley, peas, beans, lentils, oats, or tapioca can be processed to form digestion-resistant soluble fiber. A digestion resistant soluble fiber includes starch linkages that cannot be hydrolyzed by enzymes of the human digestive tract. Soluble fiber used in a nicotine lozenge provided herein can be a soluble fiber generally recognized as safe ("GRAS") by the Food and Drug Administration or another appropriate private, state, or national regulatory agency.

A nicotine lozenge provided herein can, in some cases, include up to 15 weight percent water. In some cases, a nicotine lozenge provided herein can include between 2 weight percent and 15 weight percent water. In some cases, a nicotine lozenge provided herein can include between 3 weight percent and 10 weight percent water. In some cases, a nicotine lozenge provided herein can include between 4 weight percent and 7 weight percent water.

Nicotine or derivatives thereof added to a nicotine lozenge provided herein can be in any suitable form. In some cases, a nicotine lozenge provided herein includes between 0.1 mg and 20 mg nicotine. In some cases, nicotine in a nicotine lozenge provided herein includes tobacco-derived nicotine. In some cases, nicotine in a nicotine lozenge provided herein includes synthetic nicotine. A nicotine lozenge provided herein, in some cases, can be substantially free of tobacco plant tissue. A nicotine lozenge provided herein can be substantially free of cellulose fibers. In some cases, a nicotine lozenge provided herein includes less than 10 weight percent of cellulose fibers.

A nicotine lozenge provided herein can include a sweetener dispersed therein. Suitable sweeteners include saccharine, sucralose, aspartame, acesulfame potassium, and combinations thereof. In some cases, a nicotine lozenge provided herein can be substantially free of sugars and sugar alcohols. For example, a nicotine lozenge can be substantially free of sugars and sugar alcohols, but include non-nutritive sweeteners. In some cases, a nicotine lozenge provided herein can include non-caramelized sugars and/or sugar alcohols in a percentage of no more than 25 weight percent. For example, mannitol and/or sorbitol can be added to reduce the glass transition temperature of a molten mixture provided herein. When included, sugars and sugar alcohols in a molten mixture form a solution with the soluble fiber. Sugars and sugar alcohols can alter the glass transition temperature of a molten mixture provided herein. When cooled below the glass transition temperature, a solution of soluble fiber and sugar alcohols remains an amorphous, single-phase, non-crosslinked structure.

A nicotine lozenge provided herein can include flavorants. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, chai, coriander, coffee, mint oils from a species of the genus *Mentha*, cocoa, and combinations thereof. Synthetic flavorants can also be used. In certain cases, a combination of flavorants can be combined to imitate a tobacco flavor. The particular combination of flavorants can be selected from flavorants that are GRAS in a particular country, such as the United States. Flavorants can also be included in the nicotine lozenge as encapsulated flavorants.

A nicotine lozenge provided herein can include a plasticizer dispersed in the soluble-fiber matrix. For example, the plasticizer can be propylene glycol, triacetin, glycerin, vegetable oil, partially hydrogenated oil, triglycerides, triacetin, or a combination thereof.

A body of a nicotine lozenge provided herein can have a variety of different shapes, some of which include disk, shield, heart, rectangle, and square. In some cases, a body of a nicotine lozenge provided herein can have rounded corners. In some cases, the body of the nicotine lozenge can be spherical. According to certain cases, the body can have a length or width of between 1 mm and 25 mm and a thickness of between 1 mm and 25 mm. In some cases, the body can have a length or width of between 5 mm and 15 mm and a thickness of between 2 mm and 5 mm. In some cases, a nicotine lozenge provided herein can include a colorant. For example, a body of a nicotine lozenge provided herein can include titanium dioxide, which can provide the body with a white color. In some cases, a coating on the body can include a colorant.

A method of forming nicotine lozenges can include forming a molten mixture of at least 40 weight percent soluble fiber, nicotine, and less than 15 weight percent water, while maintaining a mixture temperature of less than 150° C. In some cases, the molten mixture includes at less than 13 weight percent, less than 10 weight percent, less than 8 weight percent, less than 7 weight percent, less than 6 weight percent, or less than 5 weight percent water. In some cases, the molten mixture includes at least 3 weight percent, at least 4 weight percent, at least 6 weight percent, or at least 7 weight percent water. In addition to nicotine, water, and soluble fiber (e.g., maltodextrin), a molten mixture provided herein can include one or more additives selected from colorants, sweeteners, flavorants, plasticizers, antioxidants, and combinations thereof. In some cases, the molten mixture is substantially free of cellulose fiber, tobacco plant tissue, and/or sugar alcohols.

In some cases, the molten mixture provided herein is formed in an extruder. The extruder can be a multi-staged extruder having different sections that are heated to different temperatures and/or have different ingredients introduced. In some cases, an extruder provided herein can include multiple stages and can be used in a method provided herein in a process where the maximum temperature in any stage is no more than 150° C. (e.g., no more than 150° C., no more than 110° C., or no more than 105° C.). In some cases, the molten mixture can be heated to a maximum temperature of greater than the molten mixture's Tg and less than 150° C.

Portioning the molten mixture provided herein can be accomplished using any suitable method. In some cases, the molten mixture can be formed into a sheet of a predetermined thickness as it comes out of the extruder and individual nicotine lozenges cut from the sheet with a stamping die. A method provided herein can further include cooling nicotine lozenges and packaging nicotine lozenges.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Nicotine lozenges described herein include nicotine or a derivative thereof in a soluble-fiber matrix. Nicotine or a derivative thereof can be dispersed in the soluble-fiber matrix such that the nicotine or derivative thereof is released from the nicotine lozenge as it dissolves when the nicotine lozenge is received within the oral cavity and exposed to saliva. The nicotine lozenges described herein can provide a favorable additive release profile and tactile experience. In some cases, a nicotine lozenge provided herein includes unbound nicotine in solution with soluble fiber of the matrix.

In addition to nicotine and/or derivatives thereof, one or more additional additives can be included in a nicotine lozenge provided herein and adapted to be released from the nicotine lozenge when the nicotine lozenge is placed in an oral cavity. In some cases, a nicotine lozenge provided herein can include a combination of nicotine, sweeteners, and flavorants to mimic the flavor profile and tactile experience of certain tobacco products.

A nicotine lozenge provided herein can take up to 1 hour to dissolve when placed in an adult consumer's mouth. In some cases, a nicotine lozenge provided herein can take between 1 minute and 30 minutes to dissolve when placed in an adult consumer's mouth if the adult consumer does not masticate the nicotine lozenge. In some cases, a nicotine lozenge provided herein can take between 2 minutes and 15 minutes to dissolve when placed in an adult consumer's mouth if the adult consumer does not masticate the nicotine lozenge.

In some cases, a nicotine lozenge can be substantially free of tobacco plant tissue. As used herein, the term "tobacco plant tissue" refers to processed or non-processed cellulosic parts (e.g., leaves, stems) of a member of the genus *Nicotiana*, but does not include extracts of tobacco (e.g., tobacco-derived nicotine). As used herein, "substantially free of tobacco plant tissue" means that the product includes less than 0.5 weight percent of tobacco plant tissue. For example, a nicotine lozenge provided herein can include one or more organoleptic components extracted from raw or processed tobacco, yet be substantially free of tobacco plant tissue. In some cases, a nicotine lozenge provided herein can include one or more organoleptic components extracted from raw or processed tobacco, yet include no tobacco plant tissue.

Nicotine lozenges provided herein can be substantially free of cellulose fibers. In some cases, a nicotine lozenge provided herein includes up to 10 weight percent cellulosic fibers. Cellulosic fibers used in a nicotine lozenge provided herein can have an average fiber size of less than 200 micrometers. In particular cases, cellulosic fibers in a nicotine lozenge provided herein have sizes between 25 and 125 micrometers.

In addition to nicotine, sweeteners, and flavorants, the nicotine lozenge can also include fillers, plasticizers, antioxidants, colorants, and/or processing aids. Fillers can also be included in the soluble-fiber matrix to alter the texture or pliability of the nicotine lozenge. The soluble-fiber matrix can also include plasticizers (e.g., propylene glycol), which can increase the softness of a nicotine lozenge provided herein. Antioxidants can be used to preserve nicotine in the nicotine lozenge. Processing aids can also be present in the nicotine lozenge and be used to facilitate shaping processes.

Nicotine Lozenge Shapes and Packaging

Figure 1:
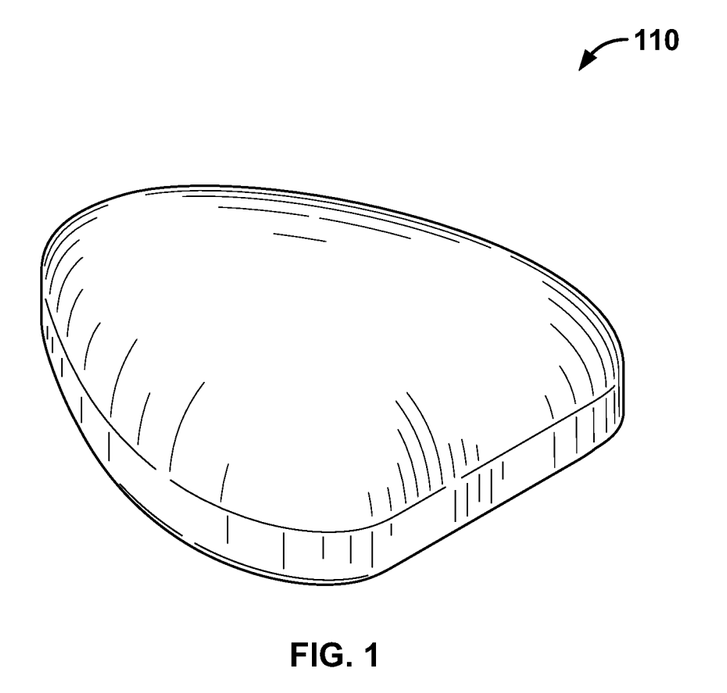
FIG. 1 is a perspective view of an exemplary nicotine lozenge provided herein.

FIG. 1 depicts an example of a nicotine lozenge 110. The nicotine lozenge 110 has a rounded shield shape. For example, nicotine lozenge 110 can have a diameter of about 16 mm, a width of 14 mm, and a thickness of about 11 mm.

Figure 1A:
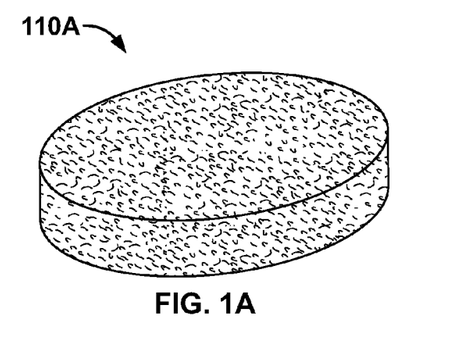
FIGS. 1A-1O illustrates various additional exemplary shapes of nicotine lozenges provided herein.
Figure 1B:
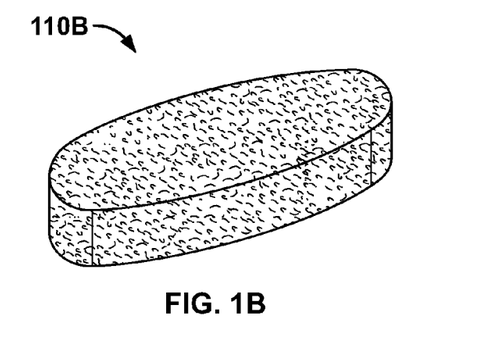
Figure 1C:
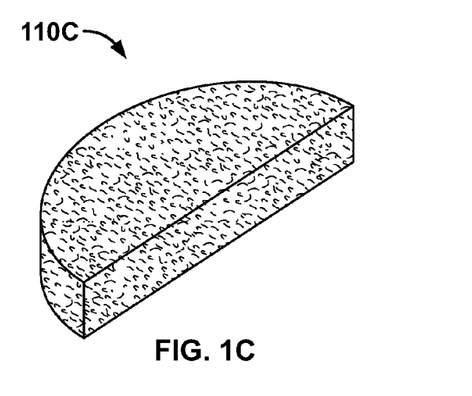
Figure 1D:
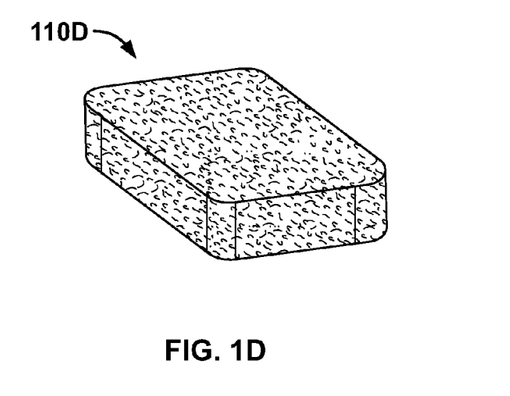
Figure 1E:
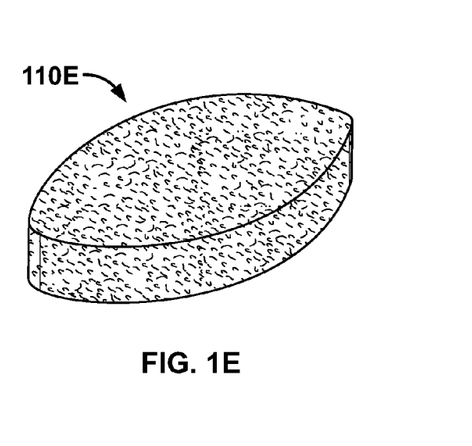
Figure 1F:
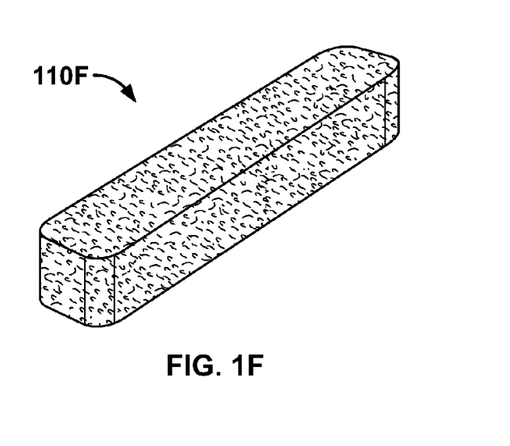
Figure 1G:
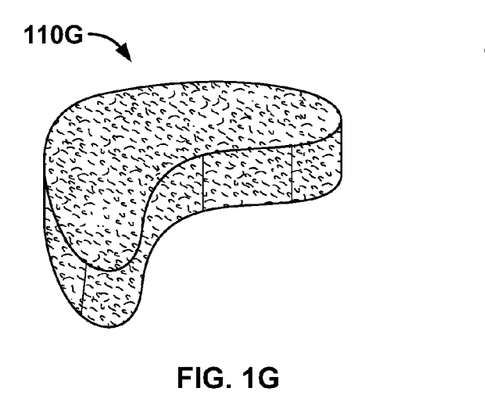
Figure 1H:
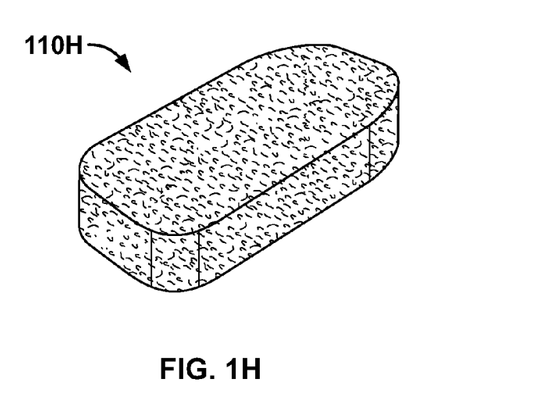
Figure 1I:
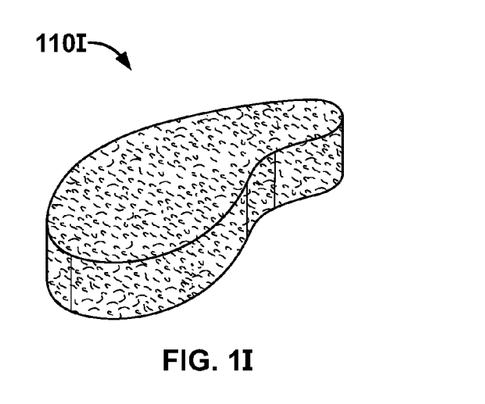
Figure 1J:
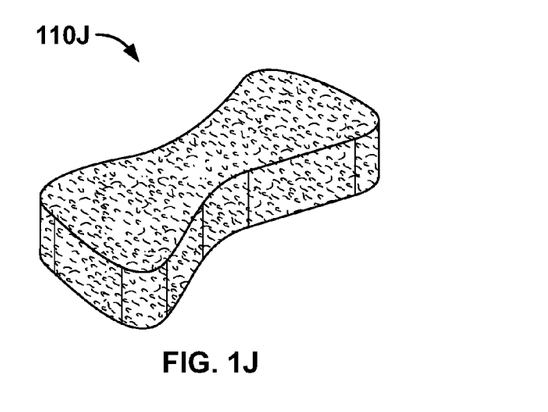
Figure 1K:
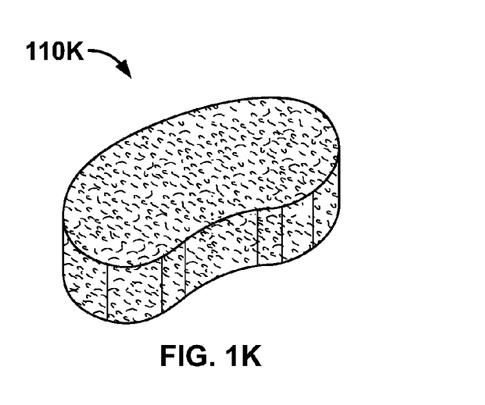
Figure 1L:
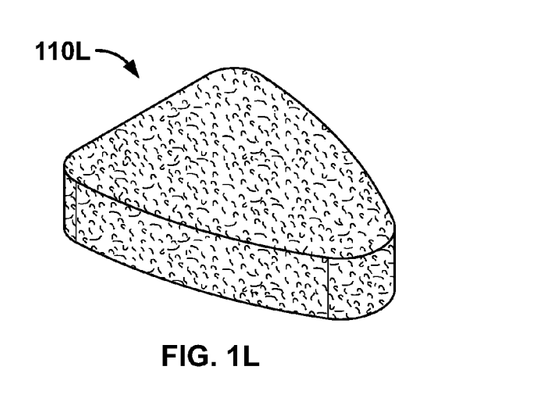
Figure 1M:
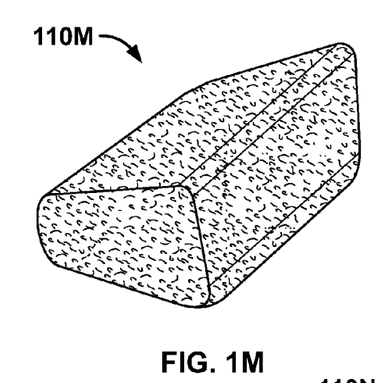

Referring now to FIGS. 1A-1N, nicotine lozenges provided herein can be molded into any desired shape. For example, referring to FIGS. 1A-1L, nicotine lozenges 110A-L can be formed in shapes that promotes improved positioning in the oral cavity, improved packaging characteristics, or both. In some circumstances, nicotine lozenges 110A-L can be configured to be: (A) an elliptical-shaped nicotine lozenge 110A; (B) an elongated elliptical-shaped nicotine lozenge 110B; (C) semi-circular nicotine lozenge 110C; (D) square or rectangular-shaped nicotine lozenge 110D; (E) football-shaped nicotine lozenge 110E; (F) elongated rectangular-shaped nicotine lozenge 110F; (G) boomerang-shaped nicotine lozenge 110G; (H) rounded-edge rectangular-shaped nicotine lozenge 110H; (I) teardrop- or comma-shaped nicotine lozenge 110I; (J) bowtie-shaped nicotine lozenge 110J; (K) peanut-shaped nicotine lozenge 110K; and (L) flat shield-shaped nicotine lozenge. Alternatively, the nicotine lozenge can have different thicknesses or dimensionality, such that a beveled article (e.g., a wedge) is produced (see, for example, product 110M depicted in FIG. 1M) or a hemi-spherical shape is produced.

Figure 1N:
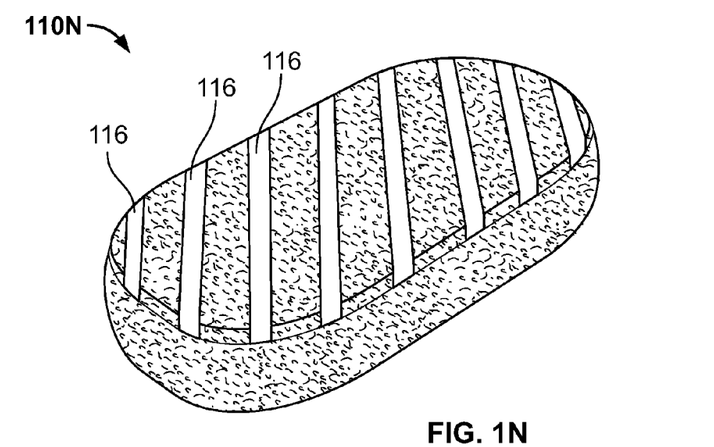

In addition or in the alternative to flavorants being included within the soluble-fiber matrix, flavorants can be included on an exterior of the nicotine lozenge 110. For example, referring to FIG. 1N, for example, some embodiments of a nicotine lozenge 110N can be equipped with flavor strips 116.

Figure 1O:
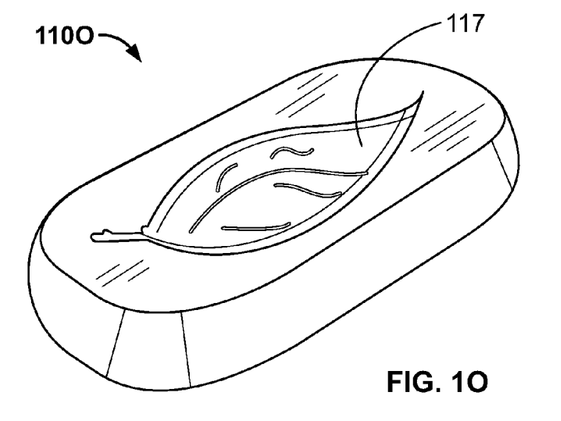

Referring to FIG. 1O, particular embodiments of the nicotine lozenge 110 can be embossed or stamped with a design (e.g., a logo, an image, or the like). For example, the nicotine lozenge 110O can be embossed or stamped with any type of design 117 including, but not limited to, a trademark, a product name, or any type of image. The design 117 can be formed directly into the nicotine lozenge, arranged along the exterior of the product 110O. The design 117 can also be embossed or stamped into those embodiments with a dissolvable film 116 applied thereto.

In some cases, the nicotine lozenge 110 or lozenges 110A-O can be wrapped or coated in an edible or dissolvable film, which may be opaque, substantially transparent, or translucent. The dissolvable film can readily dissipate when the nicotine lozenge 110 is placed in an oral cavity. In some cases, the nicotine lozenge 110 can be coated with a mouth-stable material. Exemplary coating materials include Carnuba wax, Beeswax, gelatin, acetylated monoglyceride, starch (e.g., native potato starch, high amylose starch, hydroxypropylated potato starch), Zein, Shellac, ethyl cellulose, methylcellulose, hydroxypropyl methylcellulose, carboxymethyl cellulose, and combinations thereof. Additives, such as miglycol, titanium dioxide, kaoline, bentonite, can be incorporated into the coating material to improve oxygen or moisture barrier and mechanical properties for the coating or film. For example, a coating can include a combination of gelatin and methylcellulose or gelatin and hydroxymethylcellulose. In some cases, the coating can contain sugar alcohols such as sorbitol, mannitol, xylitol, erythritol), disaccharide-derived (e.g., isomalt, lactitol, maltitol), or polysaccharide-derived mixtures (e.g., maltitol syrup, hydrogenated starch hydrolysates [HSH]) or combinations thereof. In some cases a coating material can contain sugar alcohols and hydroxymethylcellulose, gelatin, wax, with additives. In some cases, a coating material can include a plasticizer. In some case, a coating can include a colorant, a flavorant, and/or a one or more of the additives discussed above. For example, a coating can include nicotine to provide a user with readily available nicotine. In some cases, the body of a nicotine lozenge provided herein can have surfaces roughened to improve the adherence of a coating. In some cases, a coating can provide a glossy or semi-glossy appearance, a smooth surface, and/or an appealing visual aesthetic (e.g., a nice color). In some cases, the coating (e.g., a Beeswax, Zein, acetylated monoglyceride, and/or hydroxypropylated potato starch coating) can provide a soft mouth feel. In some cases, the coating (e.g., a methylcellulose, hydroxypropyl methylcellulose, carboxymethyl cellulose, ethyl cellulose, and/or gelatin coating) can provide a hard outer coating.

One or more nicotine lozenges 110 can be packaged in a variety of conventional and non-conventional manners. For example, a plurality of nicotine lozenges 110 can be packaged in a container having a lid. In some cases, a plurality of nicotine lozenges 110 can be stacked and packaged in a paper, plastic, and/or aluminum foil tube. The packaging can have a child-resistant lid.

Nicotine Lozenge Properties

The nicotine lozenge 110 can provide a favorable tactile experience (e.g., mouth feel). The nicotine lozenge 110 can also retain its shape during processing, shipping, handling, and optionally while placed in the mouth. In some cases, the nicotine lozenge 110 can be rigid. In some cases, a nicotine lozenge 110 can be brittle such that an adult consumer can crunch or masticate the nicotine lozenge 110 in the adult consumer's mouth. A nicotine lozenge 110 provided herein can be non-porous. Manipulation of a nicotine lozenge 110 provided herein to increase the exposure of surfaces to saliva can accelerate a dissolution rate.

A nicotine lozenge 110 provided herein can have a glass transition temperature (Tg) that is in the range of 50° C. to 120° C. (i.e., about 122° F. to about 248° F.), depending on formulations (e.g. soluble fiber type and weight percentage, water content, total flavor weight percentage, etc.) and processing conditions used to form the nicotine lozenge 110. The Tg can impact the preferred operating temperature used to form a solution of the soluble fiber, nicotine, and other ingredients. By changing the soluble fiber weight percentage and type, the Tg range can be altered. In some cases, when a nicotine lozenge provided herein is placed in an adult consumer's mouth, the nicotine lozenge is not soft, but remains as an amorphous glassy state, as the adult consumer's body temperature is below the glass transition temperature range of the product. Nicotine lozenges provided herein can remain in a glassy state throughout the duration of its shelf life (e.g., at least 2 months, at least 6 months, at least 1 year, or at least 2 years). The Tg temperature can also impact a sensorial experience provided by a nicotine lozenge provided herein. For example, a glass transition temperature above body temperature can impede a nicotine lozenge from becoming sticky when placed in the adult consumers' mouth.

A nicotine lozenge 110 provided herein can have any desirable color. In some cases, a nicotine lozenge 110 provided herein can be translucent and have an off-white color. In some cases, a colorant can be included to provide a desired visual appearance. In some cases, natural and artificial colorants can be added to a soluble-fiber matrix of a nicotine lozenge 110. In some cases, a colorant can make a body of a nicotine lozenge opaque. For example, titanium dioxide can be added to a soluble-fiber matrix to produce an opaque white nicotine lozenge. Encapsulated flavors can be added during the extrusion process to create speckles, patterns or dots within the nicotine lozenge or on a surface of a nicotine lozenge 110. In some cases, a coating applied to a body of a nicotine lozenge can provide a desirable color.

A nicotine lozenge as described herein was made using about 80-85 weight percent Fibersol®-2 digestion resistant maltodextrin; between 6-7 weight percent water; and other ingredients that included nicotine, flavors, sweeteners, antioxidants, colorant, plasticizer, and processing aides. A test of the nicotine lozenge demonstrated that nicotine degradants and impurities after sixteen weeks were non-detectable. For example, as shown in Table 1, all nicotine degradants at week 16 were non-detectable under controlled conditions of 25° C., 65% relative humidity, and atmospheric pressure.

TABLE 1

% Relative to Nicotine Concentration of Nicotine Lozenge at week 16 (Average, n = 3)

| Myosmine | Nornicotine | Anabasine | Cotinine | Anatabine | Nicotine Oxide | b-Nicotyrine |
|---|---|---|---|---|---|---|
| ND | ND | ND | ND | ND | ND | ND |

Figure 2:
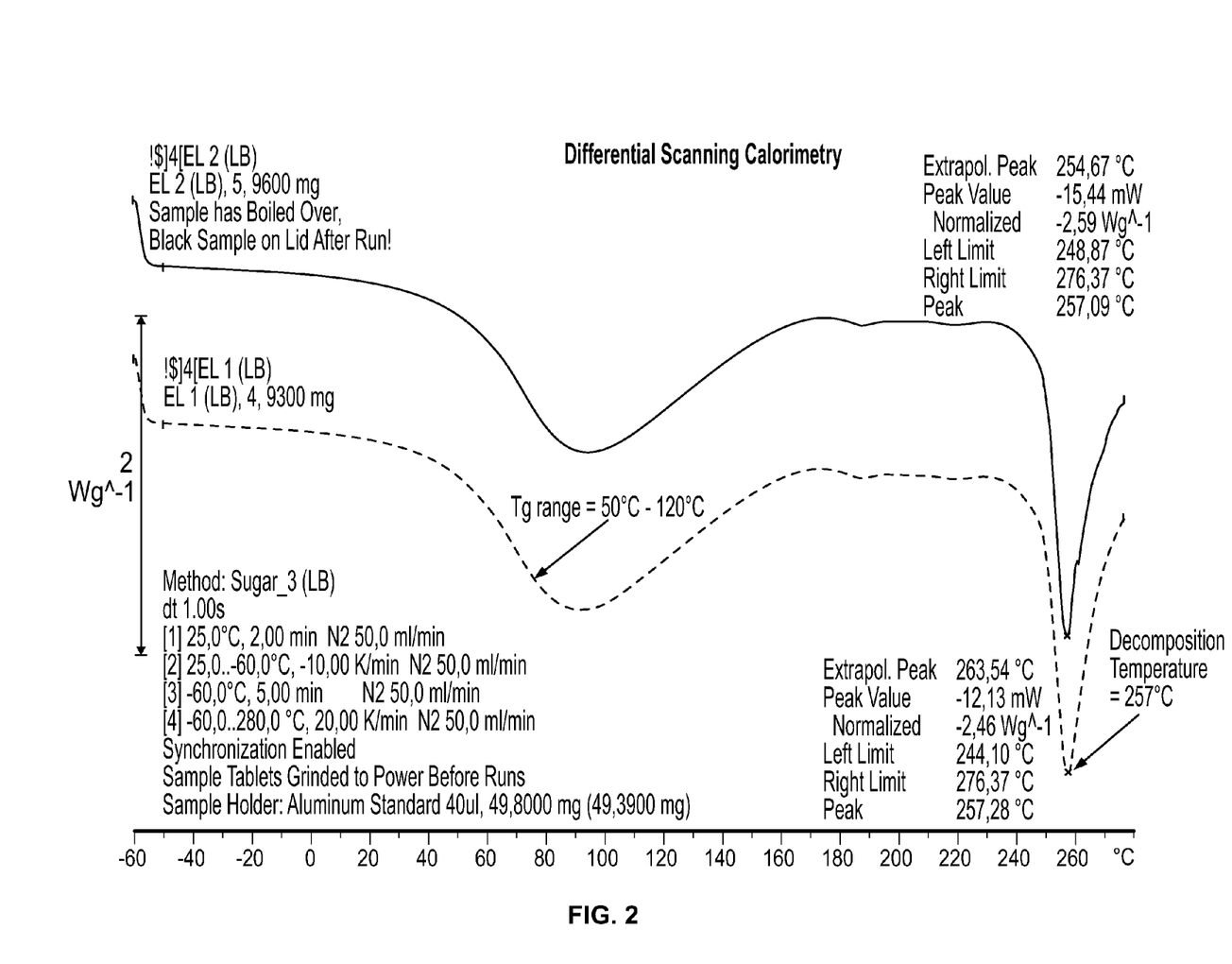
FIG. 2 is a differential scanning calorimetry data for an exemplary molten mixture provided herein.
Figure 2A:
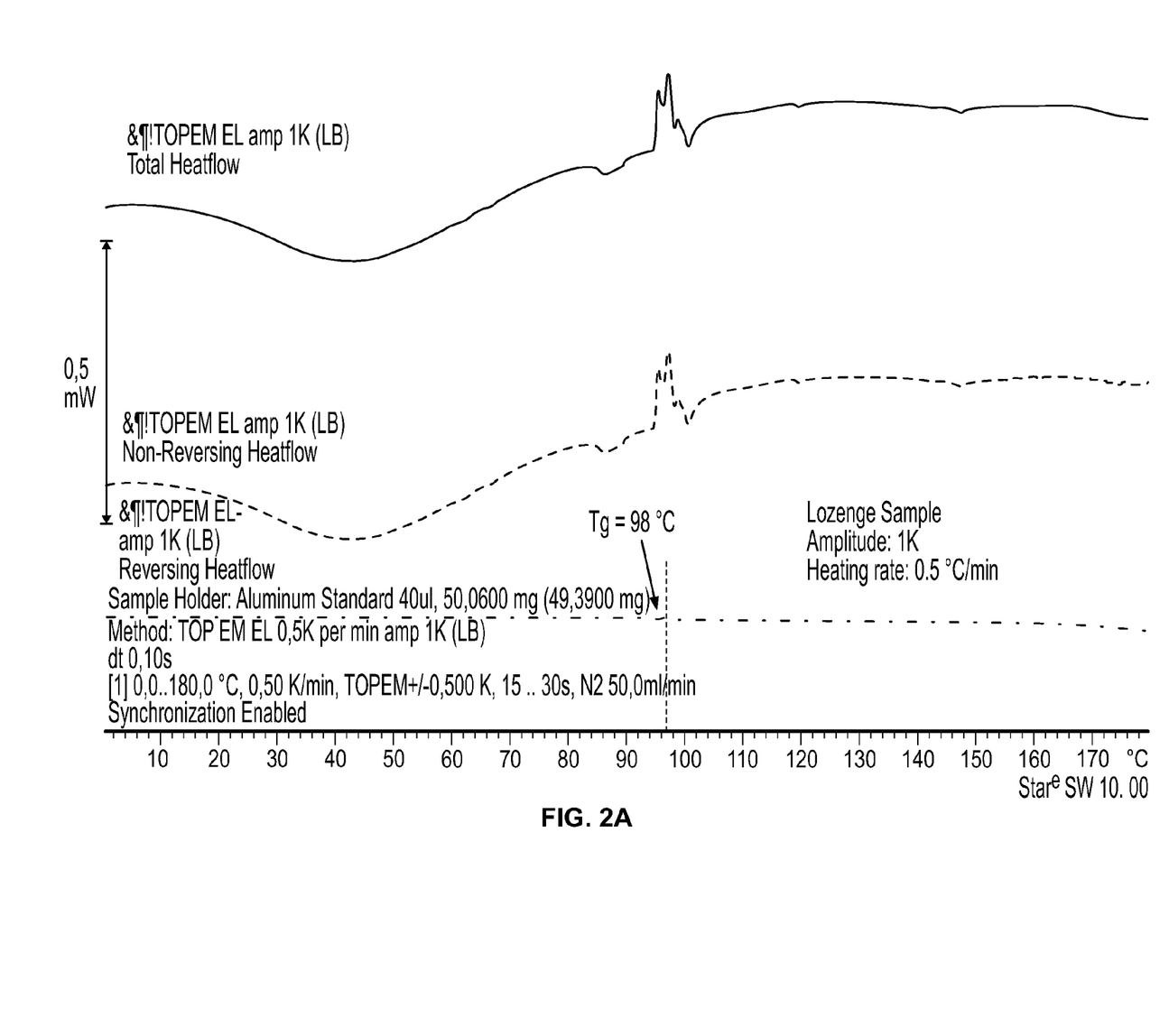
FIG. 2A is a modulated differential scanning calorimetry data for an exemplary molten mixture provided herein.
Figure 3A:
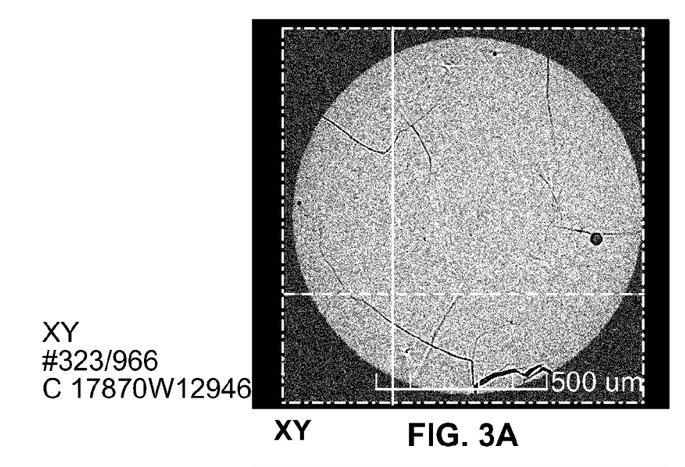
FIGS. 3A-3D depicts X-ray microtomography images from an exemplary extruded nicotine lozenge provided herein.
Figure 3B:
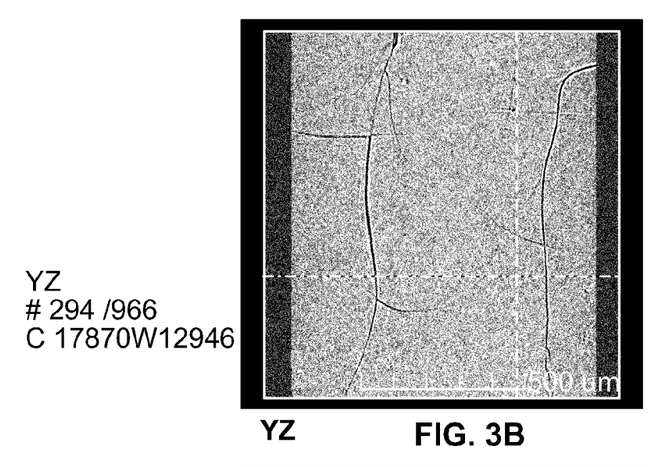
Figure 3C:
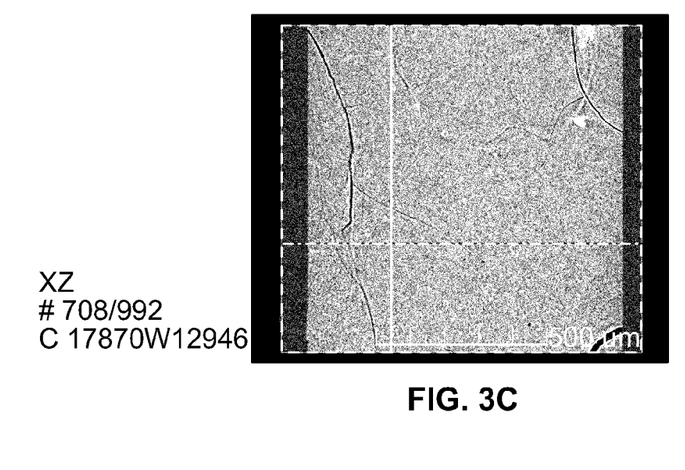
Figure 3D:
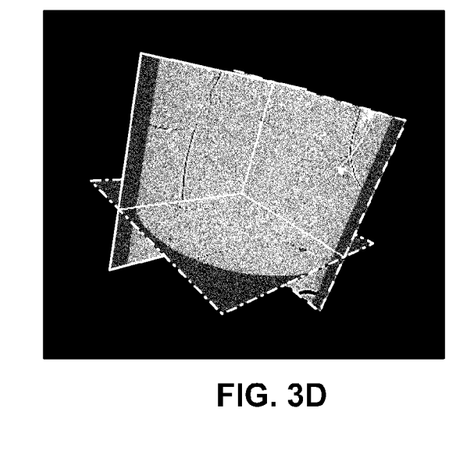

FIG. 2 shows a differential scanning calorimetry (DSC) data for an exemplary molten mixture provided herein, a nicotine lozenge that has a Tg range of between 50° C. and 120° C. By having the lower limit of the Tg range higher than body temperature (i.e., about 37° C.), nicotine lozenges provided here can remain rigid and non-sticky when placed in an adult consumer's mouth. A Tg temperature for a particular molten mixture can guide a preferred operating temperature range for the extrusion process. The process is designed to stay well below the decomposition temperature of ~257° C. as measured by DSC (See FIG. 2). One component of the mixtures that affects Tg range is the soluble fiber weight percentage and type. For example, FIG. 2A depicts the modulated DSC for an exemplary mixture, provided herein, which shows a Tg for a nicotine lozenge body that has a Tg of 98° C. By changing the soluble fiber weight percentage and type, the Tg range can be altered. When a nicotine lozenge provided herein is placed in an adult consumer's mouth, a nicotine lozenge can remain as an amorphous glassy state, as the body temperature is below the glass transition temperature range of the nicotine lozenge provided herein. A nicotine lozenge provided herein can be designed to remain in a glassy state throughout the duration of its shelf life for the product. In some cases, a nicotine lozenge provided herein can have a Tg that impacts the sensorial experience. For example, a nicotine lozenge provided herein having a Tg range greater than body temperature and can remain non-sticky when placed in an adult consumer's mouth.

The structure can be non-porous. FIGS. 3A-3D depict X-ray microtomography images from an exemplary extruded nicotine lozenge provided herein, which shows that the structure is non-porous.

Figure 4:
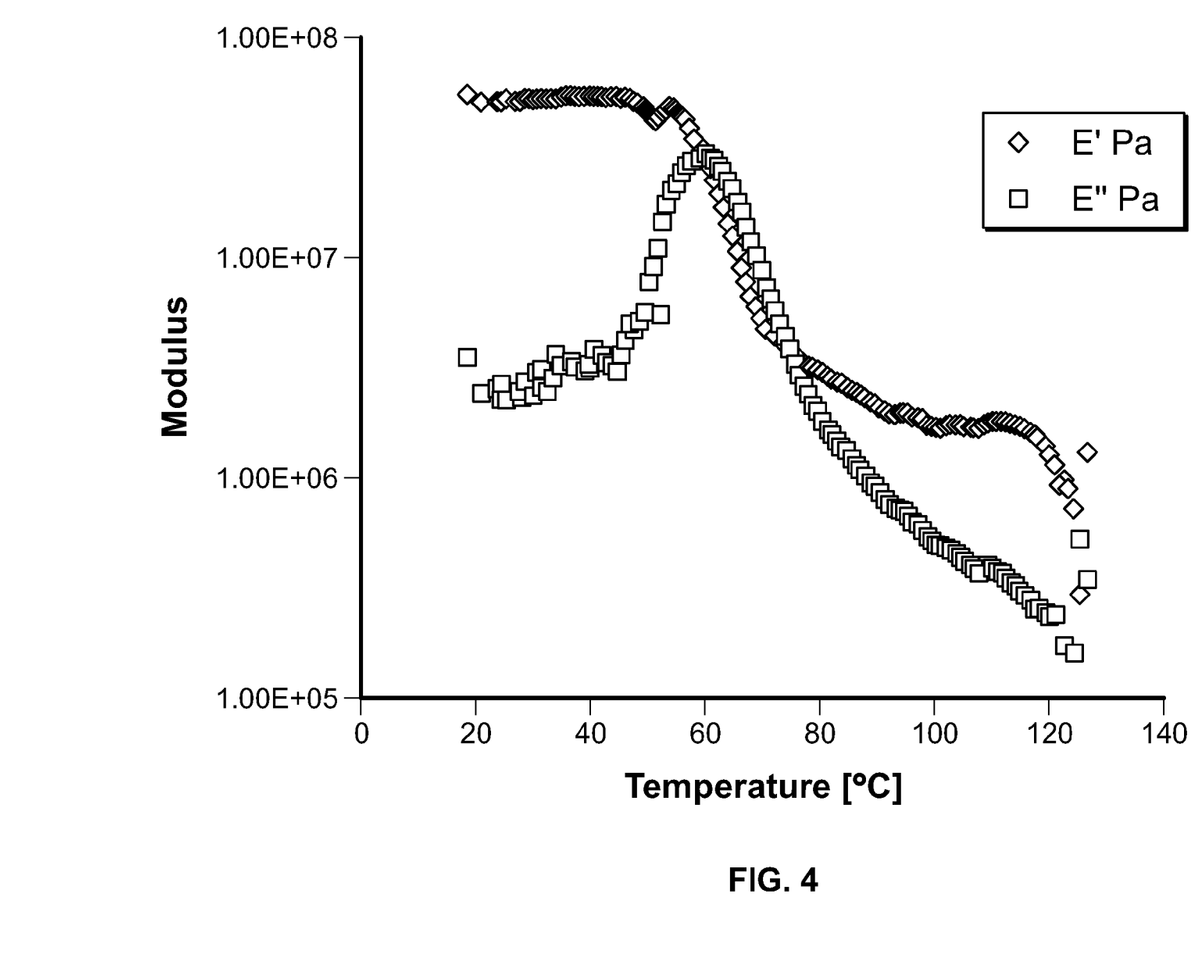
FIG. 4 is a dynamic mechanical analysis (DMA) of an exemplary extruded nicotine lozenge provided herein.

FIG. 4 is a dynamic mechanical analysis (DMA) of an exemplary extruded nicotine lozenge provided herein. The storage modulus (blue line, diamond legend) is correlated to the stiffness (E') of the material and this informs where the mixture viscosity is sufficiently pliable for processing (i.e. rubbery state). The extrusion temperature operating range is between 100° C. and 150° C.

Soluble Fibers

Soluble fiber dissolves in water at ambient temperature. Insoluble fiber does not dissolve in water at ambient temperature. Soluble fibers can attract water and form a gel. Not only are many soluble fibers safe for consumption, but some soluble fibers are used as a dietary supplement. As a dietary supplement, soluble fiber can slow down digestion and delay the emptying of a stomach. Instead of using soluble fiber as a mere additive, however, nicotine lozenges provided herein include a matrix of soluble fiber, which can dissolve to provide access to nicotine (and optionally other additives) included in the soluble-fiber matrix.

Any suitable soluble fiber or combination of soluble fibers can be used to form a soluble-fiber matrix provided herein. Suitable soluble fibers include maltodextrin, *psyllium*, pectin, guar gum, gum arabic, inulin, arabinoxylans, cellulose, and many other plant components such as resistant starch, resistant dextrins, lignin, pectins, beta-glucans, and oligosaccharides or a combination thereof. In some cases, a nicotine lozenge provided herein can include a digestion-resistant soluble fiber. A digestion resistant soluble fiber can include starch linkages that remain undigested by enzymes of the human digestive tract. In some cases, a nicotine lozenge provided herein can include a digestion-resistant maltodextrin. In some cases, a digestion-resistant maltodextrin can be derived from maze. Suitable maltodextrins can include those that are soluble in water up to 70% at 20° C., have a viscosity of about 15 cps for a 30% solution at 30° C., a DE in the range of about 6-16, and contain random $\alpha$-1,2, $\alpha$-1,3, $\alpha$-1,4, $\beta$-1,2, $\beta$-1,3 and $\beta$-1,4 glucose linkages in addition to the normal $\alpha$-1,4 glucose linkages found in partially hydrolyzed starch. See, e.g., U.S. Pat. Nos. 5,410,035; 5,380,717, which are hereby incorporated by reference. For example, Fibersol®-2 is a maltodextrin of DE 6-10 processed from corn starch using hydrochloric acid and enzymes, which can be used as the soluble fiber in a nicotine lozenge provided herein. Fibersol®-2 is partially indigestible because human digestive enzymes are incapable of digesting $\beta$ 1,2, $\beta$ 1,3 and $\beta$ 1,6 glucose bonds. See, e.g., U.S. Pat. No. 6,203,842. Other starch sources such as potato, rice, wheat, barley, peas, beans, lentils, oats, or tapioca can be processed to form digestion-resistant soluble fiber. A digestion resistant soluble fiber includes starch linkages that cannot be hydrolyzed by enzymes of the human digestive tract. In some cases, suitable soluble fibers include Pinefiber, Pinefiber C, Dexflow and Pineflow as discussed in U.S. Pat. No. 5,236,719, which is hereby incorporated by reference. Soluble fiber used in a nicotine lozenge provided herein can be GRAS by the Food and Drug Administration or another appropriate private, state, or national regulatory agency.

A nicotine lozenge body can include at least 40 weight percent of soluble fiber, at least 50 weight percent of soluble fiber, at least 60 weight percent of soluble, at least 70 weight percent of soluble fiber, at least 75 weight percent of soluble fiber, at least 80 weight percent of soluble fiber, at least 85 weight percent of soluble fiber, at least 90 weight percent of soluble fiber, or at least 95% weight percent of soluble fiber. In some cases, a nicotine lozenge body can include at least 40 weight percent maltodextrin, at least 50 weight percent maltodextrin, at least 60 weight percent maltodextrin, at least 70 weight percent maltodextrin, at least 75 weight percent maltodextrin, at least 80 weight percent maltodextrin, at least 85 weight percent maltodextrin, at least 90 weight percent maltodextrin, or at least 95 weight percent maltodextrin. In some cases, a nicotine lozenge body can include less than 95 weight percent less than 90 weight percent maltodextrin, less than 85 weight percent maltodextrin, or less than 80 weight percent maltodextrin. In some cases, a nicotine lozenge body can include at least 40 weight percent digestion-resistant maltodextrin, at least 50 weight percent digestion-resistant maltodextrin, at least 60 weight percent digestion-resistant maltodextrin, at least 70 weight percent digestion-resistant maltodextrin, at least 75 weight percent digestion-resistant maltodextrin, at least 80 weight percent digestion-resistant maltodextrin, at least 85 weight percent digestion-resistant maltodextrin, at least 90 weight percent digestion-resistant maltodextrin, or at least 95 weight percent digestion-resistant maltodextrin.

Nicotine

Nicotine within a nicotine lozenge provided herein can be tobacco-derived nicotine, synthetic nicotine, or a combination thereof. In some cases, the nicotine can be liquid nicotine. Liquid nicotine can be purchased from commercial sources, whether tobacco-derived or synthetic. In some cases, a nicotine lozenge provided herein includes between 0.1 mg and 20.0 mg of nicotine. In some cases, a nicotine lozenge provided herein includes between 0.5 mg and 10.0 mg of nicotine. In some cases, a nicotine lozenge provided herein includes between 1.0 mg and 3.0 mg of nicotine.

Tobacco-derived nicotine can include one or more other tobacco organoleptic components other than nicotine. The tobacco-derived nicotine can be extracted from raw (e.g., green leaf) tobacco and/or processed tobacco. Processed tobaccos can include fermented and unfermented tobaccos, dark air-cured, dark fire cured, burley, flue cured, and cigar filler or wrapper, as well as the products from the whole leaf stemming operation. The tobacco can also be conditioned by heating, sweating and/or pasteurizing steps as described in U.S. Publication Nos. 2004/0118422 or 2005/0178398. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. By processing the tobacco prior to extracting nicotine and other organoleptic components, the tobacco-derived nicotine may include ingredients that provide a favorable experience. The tobacco-derived nicotine can be obtained by mixing cured tobacco or cured and fermented tobacco with water or another solvent (e.g., ethanol) followed by removing the insoluble tobacco material. The tobacco extract may be further concentrated or purified. In some cases, select tobacco constituents can be removed. Nicotine can also be extracted from tobacco in the methods described in the following patents: U.S. Pat. Nos. 2,162,738; 3,139,436; 3,396,735; 4,153,063; 4,448,208; and 5,487,792.

The nicotine can also be purchased from commercial sources, whether tobacco-derived or synthetic. In some cases, a nicotine lozenge provided herein can include a derivative of nicotine (e.g., a salt of nicotine).

Liquid nicotine can be pure, substantially pure, or diluted prior to mixing it with the soluble fiber. A diluting step is optional. In some cases, liquid nicotine is diluted to a concentration of between 1 weight percent and 75 weight percent prior to mixing the liquid nicotine with the soluble fiber. In some cases, liquid nicotine is diluted to a concentration of between 2 weight percent and 50 weight percent prior to mixing the liquid nicotine with the soluble fiber. In some cases, liquid nicotine is diluted to a concentration of between 5 weight percent and 25 weight percent prior to mixing the liquid nicotine with the soluble fiber. For example, liquid nicotine can be diluted to a concentration of about 10 weight percent prior to mixing the liquid nicotine with the soluble fiber.

Additional Additives

A variety of additives other than nicotine or derivatives thereof can be included in a nicotine lozenge provided herein. The additives can include non-nicotine alkaloids, minerals, vitamins, dietary supplements, nutraceuticals, energizing agents, soothing agents, coloring agents, amino acids, chemsthetic agent, antioxidants, food grade emulsifiers, pH modifiers, botanicals (e.g., green tea), teeth whitening (e.g., SHMP), therapeutic agents, sweeteners, flavorants, and combinations thereof. In some cases, the additives can further include one or more non-nutritive sweeteners, one or more antioxidants, and one or more flavorants. With certain combinations of nicotine, sweeteners, and flavorants, a nicotine lozenge provided herein may provide a flavor profile and tactile experience similar to certain tobacco products.

Antioxidants

A nicotine lozenge 110 provided herein can include one or more antioxidants. Antioxidants can result in a significant reduction in the conversion of nicotine into nicotine-N-oxide when compared to nicotine products without antioxidants. In some cases, a nicotine lozenge provided herein can include 0.01 and 5.00 weight percent antioxidant, between 0.05 and 1.0 weight percent antioxidant, between 0.10 and 0.75 weigh percent antioxidant, or between 0.15 and 0.5 weight percent antioxidant. Suitable examples of antioxidants include ascorbyl palmitate (a vitamin C ester), BHT, ascorbic acid (Vitamin C), and sodium ascorbate (Vitamin C salt). In some cases, monosterol citrate, tocopherols, propyl gallate, tertiary butyl-hydroquinone (TBHQ), butylated hydroxyanisole (BHA), Vitamin E, or a derivative thereof can be used as the antioxidant. For example, ascorbyl palmitate can be the antioxidant in the formulations listed in Table I. Antioxidants can be incorporated into the soluble-fiber matrix (e.g., maltodextrin) during a mixing process (e.g., added to an extruder mixing the ingredients).

Sweeteners

A variety of synthetic and/or natural sweeteners can be used as additives in a nicotine lozenge 110 provided herein. Suitable natural sweeteners include sugars, for example, monosaccharides, disaccharides, and/or polysaccharide sugars, and/or mixtures of two or more sugars. In some cases, a nicotine lozenge 110 provided herein includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. A nicotine lozenge provided herein an also include non-nutritive sweeteners. Suitable non-nutritive sweeteners include: stevia, saccharin; aspartame; sucralose; or acesulfame potassium.

Flavorants

The nicotine lozenge provided herein can optionally include one or more flavorants. The flavorants can be natural or artificial. For example, suitable flavorants include wintergreen, cherry and berry type flavorants, various liqueurs and liquors (such as Dramboui, bourbon, scotch, and whiskey) spearmint, peppermint, lavender, cinnamon, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, chai, coriander, coffee, liquorish, and mint oils from a species of the genus *Mentha*, and encapsulated flavors. Mint oils useful in particular embodiments of a nicotine lozenge 110 provided herein include spearmint and peppermint. Synthetic flavorants can also be used. In some cases, a combination of flavorants can be combined to imitate a tobacco flavor. The particular combination of flavorants can be selected from flavorants that are GRAS in a particular country, such as the United States. Flavorants can also be included in the nicotine lozenge as encapsulated flavorants.

In some cases, the flavorants in a nicotine lozenge provided herein are limited to less than 20 weight percent in sum. In some cases, the flavorants in the nicotine lozenge 110 are limited to be less than 10 weight percent in sum. For example, certain flavorants can be included in the nicotine lozenge 110 in amounts of about 1 weight percent to 5 weight percent.

Cellulosic Fibers

Nicotine lozenges provided herein can optionally include cellulosic fibers within the soluble-fiber matrix. In some cases, nicotine lozenges 110 provided herein are substantially free of cellulosic fibers. As used here, "substantially free of cellulosic fibers" means that a nicotine lozenge provided herein has less than 0.5 weight percent cellulosic fibers. In some cases, nicotine lozenges 110 provided herein include up to 10 weight percent cellulosic fibers. Cellulosic fibers can be mixed with molten mixtures including soluble fibers to form a nicotine lozenge provided herein. Additives can be absorbed in cellulosic fibers. In some cases, the fibers are hydrophilic such that water-soluble additives can be wicked by the fibers. Cellulosic fibers can be derived from plant tissue. Suitable sources for cellulosic fibers include wood pulp, cotton, sugar beets, bran, citrus pulp fiber, switch grass and other grasses, *Salix* (willow), tea, and *Populus* (poplar). In some cases, the cellulosic fibers can be plant tissue comprising various natural flavors, sweeteners, or active ingredients. Cellulosic fibers can have a variety of dimensions. In some cases, cellulosic fibers in a nicotine lozenge 110 provided herein can be processed to have an average fiber size of less than 200 micrometers. In some cases, cellulosic fibers in a nicotine lozenge 110 provided herein have an average fiber length of between 25 and 125 micrometers. In some cases, cellulosic fibers are processed to have a size of 75 micrometers or less.

Plasticizers

A nicotine lozenge 110 provided herein can also include one or more plasticizers. Suitable plasticizers include propylene glycol, triacetin, glycerin, vegetable oil, partially hydrogenated oil, and medium chain triglycerides. Esters of polycarboxylic acids with linear or branched aliphatic alcohols of moderate chain length can also be used as plasticizers (OK) Moreover, plasticizers can facilitate the extrusion processes described below. In some cases, a nicotine lozenge 110 provided herein can include up to 20 weight percent plasticizer. In some cases, the nicotine lozenge 110 includes between 0.05 and 10 weight percent plasticizer, a nicotine lozenge 110 provided herein can include between 1 and 8 weight percent plasticizer, or between 2 and 4 weight percent plasticizer.

Other Additives

A nicotine lozenge provided herein may optionally include other additives. For example, these additives can include non-nicotine alkaloids, dietary minerals, vitamins, dietary supplements, therapeutic agents, and fillers. For example, suitable vitamins include Vitamins A, B1, B2, B6, C, D2, D3, E, F, and K. For example, a nicotine lozenge 110 provided herein can include C-vitamins. Suitable dietary minerals include calcium (as carbonate, citrate, etc.) or magnesium (as oxide, etc.), chromium (usually as picolinate), and iron (as bisglycinate). One or more dietary minerals could be included in a nicotine lozenge with or without the use of other additives. Other dietary supplements and/or therapeutic agents can also be included as additives.

A nicotine lozenge provided herein can also include fillers such as starch, di-calcium phosphate, lactose, sorbitol, mannitol, and microcrystalline cellulose, calcium carbonate, dicalcium phosphate, calcium sulfate, clays, silica, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, crosslinked PVP), pH stabilizers, or preservatives. In some cases, the amount of filler in the nicotine lozenge 110 is limited to less than 10 weight percent in sum. In some cases, the amount of filler in the nicotine lozenge 110 is limited to be less than 5 weight percent in sum. In some cases, the fillers are mouth stable. In some cases, the fillers can dissolve or disintegrate during use and thus result in a nicotine lozenge that becomes more pliable during use.

Production and Example

The nicotine lozenge 110 can be produced by forming a molten mixture of soluble fiber, water, and nicotine under controlled heating conditions such that a solution of soluble fiber, water, and nicotine is formed without degrading the nicotine or the soluble fiber. In some cases, a temperature of the molten mixture is maintained at a temperature below 150° C. The molten mixture is then portioned into individual nicotine lozenges. Unlike many traditional lozenges, sugar and sugar alcohols are not required to obtain a firm smooth-dissolving texture in processes provided herein. Traditional lozenges can rely on the crosslinking of sugars or sugar alcohols due to caramelization caused by heating to caramelization temperatures. Caramelization temperatures, however, can degrade nicotine. A soluble-fiber matrix, however, can provide a nicotine lozenge provided herein with a suitable dissolution time when placed in an adult consumer's mouth.

Figure 5:
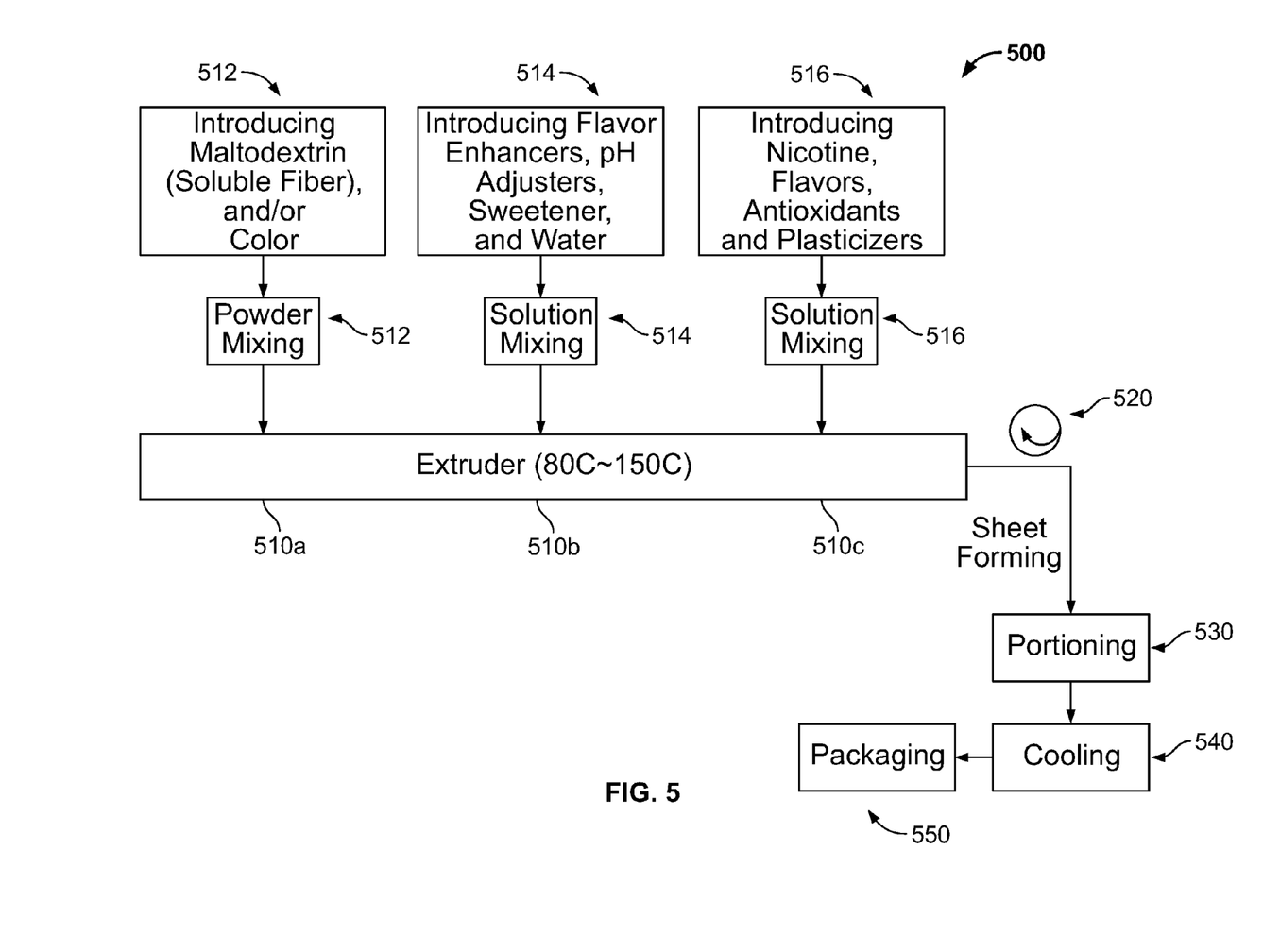
FIG. 5 depicts an exemplary process flow diagram for making nicotine lozenges provided herein.

A molten mixture can be mixed and heated in any suitable but controlled method. In some cases, such as shown in FIG. 5, ingredients for a molten mixture can be combined in an extruder and mixed in a continuous extrusion process. Unlike a traditional cooking method for many typical lozenges, a nicotine lozenge provided herein can have attributes precisely controlled by extruder operation parameters, such as feed rate, barrel temperature profile, screw design, rpms, etc.

Referring to FIG. 5, an exemplary method 500 for making nicotine lozenges provided herein can include adding dry ingredients 512 of soluble fiber (e.g., maltodextrin) and color (e.g., $TiO_2$) to a first station 510a of an extruder 510, adding a first group of solution ingredients 514, including water and sweetener, at a second station 510b, and adding a second group of solution ingredients 516, including nicotine, at a third station 510c. A mixing extruder 510 can include multiple stages controlled to be maintained at a predetermined temperature. As shown in FIG. 5, extruder 510 can include stages having temperatures ranging between 80° C. and 150° C. For example, dry ingredients 512 and a first group of solution ingredients 514 can be mixed in a first stage of extruder 510 at a temperature of between 100° C. and 120° C., one or more subsequent stages can have a higher temperature (e.g., between 120° C. and 150° C.). Second group of solution ingredients 516, including nicotine, can be added downstream of the mixture of water with the soluble fiber. Adding certain ingredients downstream can limit degradation of certain ingredients (e.g., nicotine) due to exposure to heat.

A glass transition temperature (Tg) of molten mixture used to make a nicotine lozenge provided herein can range from 50° C. to 120° C. (i.e., about 122° F. to about 248° F.). FIG. 2, discussed above, is a DSC Chart for an exemplary molten mixture that has a Tg range of between 50° C. and 120° C. FIG. 2A depicts the modulated DSC for an exemplary mixture, provided herein, which shows a Tg for a nicotine lozenge body that has a Tg of 98° C.

A water content of a nicotine lozenge provided herein can be controlled in the extrusion process to ensure that the molten mixture has a glass transition temperature of greater than human body temperature. In some cases, a molten mixture can have a water content of less than 15 weight percent. In some cases, water content in a nicotine lozenge provided herein ranges from 2 weight percent to 15 weight percent. In some cases, water content in a nicotine lozenge provided herein ranges from 2 weight percent to 20 weight percent.

After passing through the extruder, a molten mixture provided herein can have a temperature of between its glass transition temperature and 150° C. In some cases, a molten mixture of between 85 and 90 weight percent digestion-resistant maltodextrin can reach a maximum temperature in an extruder of between 100° C. and 150° C. and exit the extruder at that temperature or lower. Because a molten mixture can remain above its glass transition temperature as it exits the extruder, the molten mixture can be reshaped after it exits the extruder. Molten mixture can pass onto a conveyor and move through a sheet forming apparatus 520. Sheet forming apparatus 520 can press the molten mixture into a sheet having a predetermined thickness. For example, a predetermined thickness can be between 2 mm and 10 mm.

Individual nicotine lozenges 110 can be cut from a sheet of molten mixture in portioning station 530. In some cases, a stamping die can cut one or more individual nicotine lozenges 110 to form a sheet. In some cases, a stamping die can press one or both sides of a sheet to both cut a nicotine lozenge and reshape edges to form rounded edges on the nicotine lozenges, such as those shown in FIG. 1. Cutting individual nicotine lozenges 110 can occur when the molten mixture is still above its Tg. Individual nicotine lozenges 110 can be cooled in a cooling station 540 and packaged in a packaging station 550.

In addition to extrusion, there are other methods for mixing and carefully controlling the temperature of a molten mixture used to form nicotine lozenges provided herein.

Other Embodiments

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A nicotine lozenge, comprising a body that is wholly receivable in an oral cavity, the body comprising:
a digestion-resistant maltodextrin matrix; and
nicotine or a salt thereof dispersed in the maltodextrin matrix such that the nicotine or salt thereof is released from the body as the body dissolves when the body is at least partially received within the oral cavity of an adult tobacco consumer and exposed to saliva.

2. The nicotine lozenge of claim 1, wherein the body comprises at least 40 weight percent digestion-resistant maltodextrin.

3. The nicotine lozenge of claim 2, wherein the body comprises at least 75 weight percent digestion-resistant maltodextrin.

4. The nicotine lozenge of claim 3, wherein the body comprises at least 95 weight digestion-resistant maltodextrin.

5. The nicotine lozenge of claim 1, wherein the digestion-resistant maltodextrin is amorphous.

6. The nicotine lozenge of claim 1, wherein the nicotine is tobacco-derived nicotine.

7. The nicotine lozenge of claim 1, wherein the nicotine is synthetic nicotine.

8. The nicotine lozenge of claim 1, wherein the nicotine lozenge is substantially free of tobacco plant tissue.

9. The nicotine lozenge of claim 1, further comprising an additive selected from the group consisting of minerals, vitamins, dietary supplements, nutraceuticals, energizing agents, soothing agents, amino acids, chemsthetic agents, antioxidants, botanicals, teeth whitening agents, therapeutic agents, and combinations thereof.

10. The nicotine lozenge of claim 1, further comprising a flavorant dispersed in the maltodextrin matrix such that the flavorant is released from the body as the body dissolves when the nicotine lozenge is placed within a mouth of an adult consumer, wherein the flavorant is selected from the group consisting of licorice, wintergreen, cherry and berry type flavorants, Dramboui, bourbon, scotch, whiskey, spearmint, peppermint, lavender, cinnamon, chai, cardamon, *apium* graveolents, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang ylang, sage, fennel, pimenta, ginger, anise, chai, coriander, coffee, mint oils from a species of the genus *Mentha*, and combinations thereof.

11. The nicotine lozenge of claim 1, wherein the body is shield shaped, wherein the body has a diameter of between 1 mm and 25 mm and a thickness of between 1 mm and 25 mm.

12. The nicotine lozenge of claim 1, wherein the body is substantially free of cellulosic fibers.

13. The nicotine lozenge of claim 1, wherein the body comprises up to 10 weight percent cellulosic fibers.

14. The nicotine lozenge of claim 1, further comprising a coating on the body.

15. The nicotine lozenge of claim 1, wherein the body comprises between 0.1 mg and 20 mg nicotine.

16. The nicotine lozenge of claim 1, wherein the body has a glass transition temperature greater than 37° C.

17. The nicotine lozenge of claim 16, wherein the body has a glass transition temperature of between 50° C. and 120° C.

18. The nicotine lozenge of claim 1, wherein the body is substantially free of sugar and sugar alcohols.

19. The nicotine lozenge of claim 1, wherein the body comprises between 2 weight percent and 15 weight percent water.

20. The nicotine lozenge of claim 1, wherein the body is non-porous.

21. The nicotine lozenge of claim 1, wherein the body is brittle.

22. The nicotine lozenge of claim 1, wherein the body comprises a colorant.

23. The nicotine lozenge of claim 1, wherein the body comprises titanium dioxide.

24. The nicotine lozenge of claim 1, wherein the body comprises an antioxidant.

25. The nicotine lozenge of claim 1, wherein the body comprises a sweetener.

26. The nicotine lozenge of claim 1, wherein the body comprises a plasticizer.

27. A nicotine lozenge, comprising a body that is wholly receivable in an oral cavity, the body comprising:
an amorphous, digestion-resistant soluble-fiber matrix comprising at least 40 weight percent soluble fiber; and
nicotine or a salt thereof dispersed in said soluble-fiber matrix such that the nicotine or salt thereof is released from the body as the body dissolves when the body is at least partially received within the oral cavity of an adult tobacco consumer and exposed to saliva.

28. The nicotine lozenge of claim 27, wherein the body comprises one or more soluble fibers selected from the group consisting of maltodextrins, *psyllium*, inulin, arabinoxylans, cellulose, resistant starch, resistant dextrins, lignin, pectins, beta-glucans, and oligosaccharides, and combinations thereof, wherein the body comprises at least 75 weight percent soluble fiber, wherein the body is substantially free of cellulosic fibers, tobacco plant tissue, sugar, and sugar alcohols, wherein the body comprises between 0.1 mg and 20 mg nicotine, and wherein the body has a glass transition temperature of between 50° C. and 120° C.

29. The nicotine lozenge of claim 27, further comprising a flavorant dispersed in said soluble-fiber matrix such that the flavorant is released from the body as the body dissolves when the nicotine lozenge is placed within a mouth of an adult consumer.

30. A method of forming nicotine lozenges:
    forming a molten mixture of digestion-resistant maltodextrin, nicotine, and water while maintaining a mixture temperature of less than 150° C., the molten mixture including at least 40 weight percent of soluble fiber and less than 15 weight percent water; and
    portioning the molten mixture into a plurality of nicotine lozenges.

31. The method of claim 30, wherein the molten mixture is formed in an extruder.

32. The method of claim 31, wherein the extruder comprises multiple stages where the maximum temperature in any stage is no more than 150° C., wherein the extruder extrudes the molten mixture at a temperature of greater than the molten mixture's Tg and less than 150° C.

33. The method of claim 31, wherein portioning the molten mixture comprises forming a sheet of a predetermined thickness of the molten mixture as it comes out of the extruder and stamping said sheet with a stamping die to form at least one nicotine lozenge having a predetermined shape.

34. The method of claim 30, wherein the molten mixture comprises at least 40 weight percent maltodextrin.

35. The method of claim 30, wherein the molten mixture further comprises one or more additives selected from the group consisting of colorants, sweeteners, flavorants, plasticizers, antioxidants, and combinations thereof; and wherein the molten mixture is substantially free of cellulose fiber, tobacco plant tissue, sugar, or sugar alcohols.

* * * * *